United States Patent [19]

Tedder et al.

[11] Patent Number: 4,987,084
[45] Date of Patent: Jan. 22, 1991

[54] METHOD OF TESTING THE EFFECT OF A MOLECULE ON B LYMPHOCYTE FUNCTION

[75] Inventors: Thomas F. Tedder, Wellesley; Stuart F. Schlossman; Haruo Saito, both of Newton, all of Mass.

[73] Assignee: Dana Farber Cancer Institute, Boston, Mass.

[21] Appl. No.: 313,108

[22] Filed: Feb. 21, 1989

[51] Int. Cl.$^5$ .................. C12Q 1/02; C12Q 1/18; G01N 33/48
[52] U.S. Cl. .................................. 436/63; 435/29; 435/32
[58] Field of Search ................. 436/63; 435/29, 32

[56] References Cited

PUBLICATIONS

Nadler et al., "B Cell Origin of Non-T Cell Acute Lymphoblastic Leukemia A Model for Discrete Stages of Neoplastic and Normal Pre-B Cell Differentiation," J. Clin. Invest. 74: 332–340 (1984).
Tedder et al., "Antibodies Reactive with the B1 Molecule Inhibity Cell Cycle Progression but not Activation of Human B lymphocytes," Eur. J. Immunol. 16: 881–887 (1986).
MacDougall et al., "Detection of Ligand-Activated Conductive Ca$^{21}$ Channels in Human B Lymphocytes," Cell 54: 229–234 (1988).
Fukishima et al., "Voltage-gated Ca$^{2+}$ Channel in Mouse Myeloma Cells," Proc. Natl. Acad. Sci. U.S.A. 80: 2240–2242 (1983).
Dugas, "Human B Cell Activation: Selective Sensitivity of the Early Stages to Calcium Channel-Blocking Drugs," Eur. J. Immunol. 16: 162–167 (1986).
Tedder et al., "The B Cell Surface Molecule B1 is Functionally Linked with B Cell Activation and Differentiation," The Journal of Immunology 135: 973–979 (1985).
Tedder et al., "Isolation and Structure of a cDNA Encoding the Bl (CD20) Cell-Surface Antigen of Human B Lymphocytes," Proc. Natl. Acad. Sci. U.S.A. 85: 208–212 (1988).
Tedder et al., "Cloning of a Complementary DNA Encoding a New Mouse B Lumphocyte Differentiation Antigen, Homologous to the Human B1 (CD20) Antigen and Localization of the Gene to Chromosome 19," The Journal of Immunology 141: 4388–4394 (1988).
Tedder et al., "Phosphorylation of the B1 (CD20) Molecule by Normal and Malignmant Human B Lymphocytes," The Journal of Biological Chemistry 263: 10009–10015 (1988).

*Primary Examiner*—Robert J. Warden
*Assistant Examiner*—Kimberly A. Trautman
*Attorney, Agent, or Firm*—Fish & Richardson

[57] ABSTRACT

A method of testing the effect of an agonist or an antagonist to B lymphocyte cell surface protein CD20 on B lymphocyte function which involves determining calcium ion flux across the B lymphocyte membrane, contacting the B lymphocyte with the agonist or antagonist, and determining the change in calcium ion flux across the membrane after exposure of the B lymphocyte to the agonist or antagonist, is described. In preferred embodiments of the method the agonist or antagonist is a ligand that binds CD20 or an antibody to CD20.

In other preferred embodiments, calcium ion flux is more preferably determined in terms of transmembrane current flow and most preferably determined in terms of the change in cytosloic CA$^{2+}$ concentration.

8 Claims, 3 Drawing Sheets

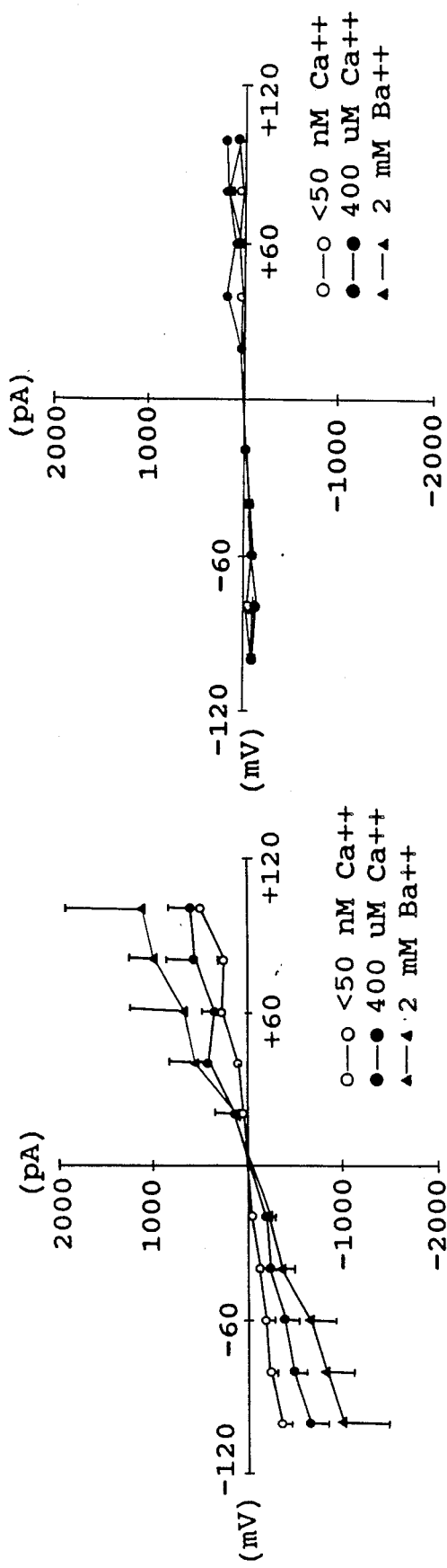

METHOD OF TESTING THE EFFECT OF A MOLECULE ON B LYMPHOCYTE FUNCTION

The invention was made with Government support, and the Government has certain rights in this invention under grants from the National Institutes of Health AI26872 and CA34183.

The invention relates to methods of testing the effects of various molecules on B lymphocyte function.

BACKGROUND OF THE INVENTION

B lymphocytes, the central component of the humoral immune response, arise from pluripotent stem cells and progress through a series of differentiation stages before final maturation into antibody-secreting plasma cells. Numerous genes are turned on and off during this progression with some of these genes being B lineage-restricted. Expression of these B cell-specific genes during differentiation ultimately determines the functional program of the B cells as B cells are activated and regulated through their cell-surface molecules. A human B lymphocyte-restricted differentiation antigen CD20 is expressed early during pre-B cell development and persists until plasma cell differentation (Nadler et al., J. Clin. Invest. 74:332 (1984)). Antibody binding to CD20, a phosphoprotein, generates a transmembrane signal which is involved in regulating B cell proliferation and differentiation. The antibody binding results in a rapid increase in phosphorylation of the CD20 molecule without an increase in intracellular $Ca^{2+}$ concentration and is believed to mediate inhibition by blocking a required step of the normal activiation process (Tedder et al., Eur. J. of Immunol. 16:881–887 (1986)).

Another kind of transmembrane signaling involves the generation of increased levels of intracellular $Ca^{2+}$ (MacDougall et al., Cell 54:229 (1988)). Ion channels in lymphocyte plasma membranes have been directly linked with activation and cell cycle progression (Fukushioma et al., Proc. Natl. Acad. Sci. USA 80:2240–2242 (1983)), and both $Ca^{2+}$ channel blocking drugs (e.g., diltiazem) and the absence of extracellular $Ca^{2+}$ prevent B cell activation (Dugas et al., Eur. J. Immunol. 16:162–167 (1986)).

SUMMARY OF THE INVENTION

In general, the invention features a method of testing the effect of an agonist or an antagonist to B lymphocyte cell surface protein CD20 on B lymphocyte function which involves determining calcium ion flux across the B lymphocyte membrane, contacting the B lymphocyte with the agonist or antagonist, and determining the change in calcium ion flux across the membrane after exposure of the B lymphocyte to the agonist or antagonist. An agonist is any agent that selectively augments CD20 function, and an antagonist is any agent that selectively inhibits CD20 function.

In another aspect, the invention features a method of testing the effect of an agonist or antagonist to B lymphocyte cell surface protein CD20 on a modified CD20 protein which involves modifying the CD20 cDNA, transforming a CD20− cell line with the modified CD20 cDNA, expressing modified CD20 protein encoded by the modified cDNA on the surface of a cell of the CD20− cell line, determining the calcium ion flux across the membrane of the transformed cell expressing the modified CD20, contacting the transformed cell with the agonist or antagonist, and determining the change in calcium ion flux across the membrane after exposure of the transformed cell to the agonist or antagonist.

In embodiments of the methods, calcium ion flux is more preferably determined in terms of transmembrane current flow and most preferably determined in terms of the change in cytosolic $Ca^{2+}$ concentration.

In one embodiment, a preferred agonist or antagonist is a ligand that binds CD20. In another embodiment, a preferred agonist or antagonist is antibody to CD20. In another preferred embodiment, B lymphocytes are contacted with antibody for at least a period of time equivalent to one cell cycle before the change in calcium ion flux is determined.

It has now been discovered that contrary to previously believed mechanisms of action of CD20 determined from antibody studies, CD20 itself is directly involved in $Ca^{2+}$ mobility, either as a $Ca^{2+}$ channel or as a regulator of conductive $Ca^{2+}$ entry across B cell membranes. The methods of the invention will permit the accurate determination of the interaction of agents with CD20 by simple indirect tests.

Abnormal B lymphocyte function is associated with most leukemias and lymphomas and many autoimmune disorders and allergies. $Ca^{2+}$ channel blocking agents attack all cells with a $Ca^{2+}$ channel and have a specific effect on malignant cells because of their faster rate of growth. Therefore, generic $Ca^{2+}$ channel blocking agents often have toxic side effects.

The connection now possible between the two separate lines of inquiry into the mechanism of B cell activation permits the development of $Ca^{2+}$ channel blocking agents which will selectively inhibit B lymphocyte function through the CD20 cell surface protein without interfering with other cells of the immune system.

Other features and advantages of the invention will be apparent from the following description of the preferred embodiments thereof and from the claims.

BRIEF DESCRIPTION OF THE DRAWINGS

In the drawings,

FIGS. 3A and 3B show transmembrane current for a specific applied voltage for transfected cells with and without the CD20 cDNA insert.

DESCRIPTION OF THE PREFERRED EMBODIMENT

Figure 1:
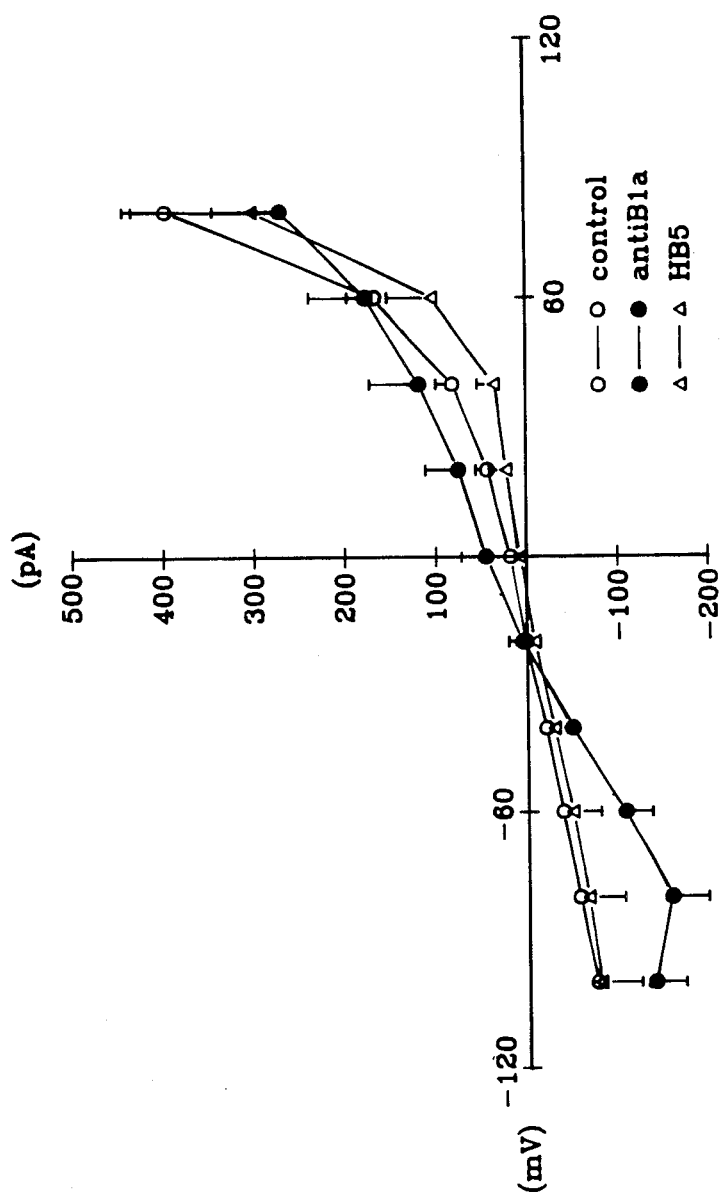
FIG. 1 shows transmembrane current for a specific applied voltage for CD20+ B lineage cells.

Transmembrane currents were examined in CD20+ Daudi lymphocytes in whole-cell voltage clamp analysis (Hamill et al., Pflugers Arch. 391:85–110 (1981)). Anti-B1 is a monoclonal antibody (Mab) against CD20 which has no acute immunological effects but prevents the G-S phase cell cycle transition in mitogen stimulated B lymphocytes (Tedder et al., supra). As shown in FIG. 1, addition of anti-B1 antibody to the bathing solution did not alter the whole cell current across Daudi lymphocyte membranes within 15 minutes. However, when Daudi lymphocytes were cultured in the presence of anti-B1 antibody for 24 h prior to whole cell clamp, significantly larger ($p<0.05$) instantaneous inward currents at hyperpolarizing test clamps were present. HB5 (a Mab to the Epstein-Barr Virus C3d receptor used as an isotype matched control for anti-B1 antibody) failed to alter the whole cell currents, either acutely or after 24 h in culture.

To isolate CD20 from other B lymphocyte specific membrane proteins, the T lymphocyte cell line, Jurkat, which does not express CD20, was transfected with CD20 cDNA, CD20+ clones were isolated, and a stable cell line expressing 10,000-20,000 anti-B1 antibody binding sites/cell was developed according to the following procedure. (A clonal line transfected with the vector without CD20 cDNA insert was also isolated as a control.)

Figure 2:
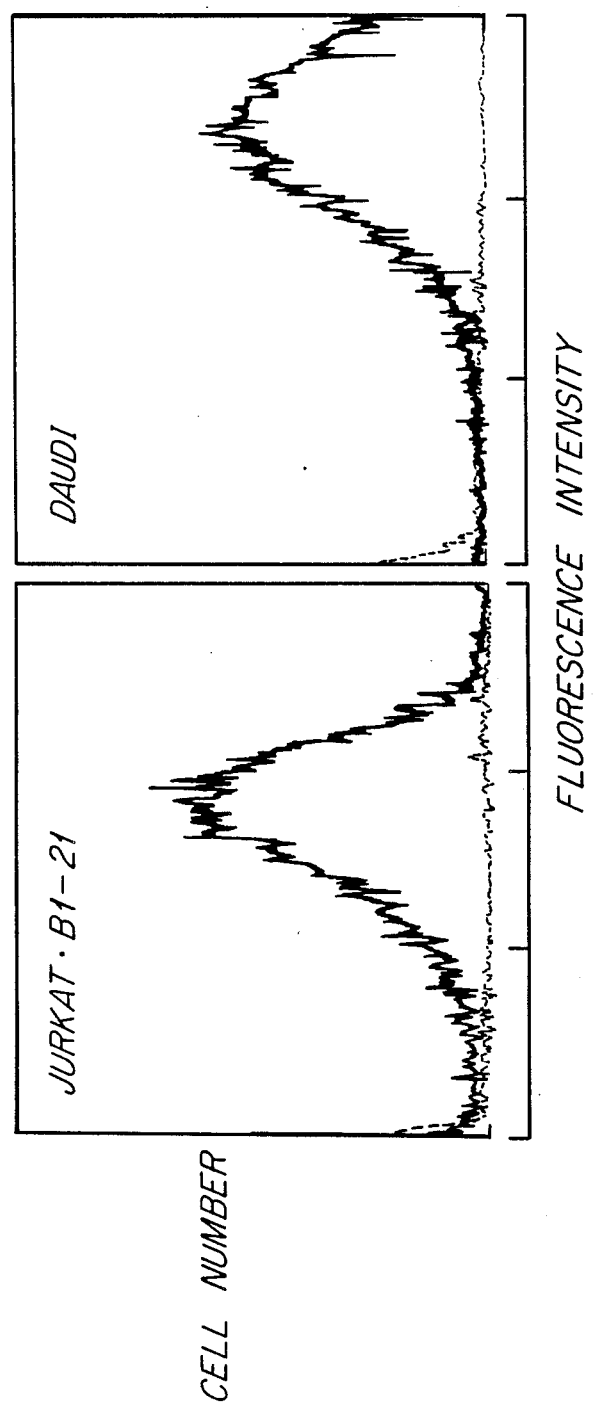
FIG. 2 shows flow cytometry analysis of CD20 expression.

As shown in FIG. 2, flow cytometry analysis revealed extensive CD20 expression in one of the isolated clones (Jurkat.B1-21 (solid line)) as compared with Jurkat cells transfected with the vector alone (dashed line). Greater than 90% of the Jurkat.B1-21 cells expressed CD20. The phenotype of Jurakat.B1 21 remained constant following transfection with CD20 cDNA, and the cells expressed all of the surface markers that the parent cell line expressed.

As shown in FIG. 3A, lowering the bath [$Ca^{2+}$] from 400 μM to 50 nM reduced the CD20-associated inward current component in CD20+ cells. Addition of 2 mM $Ba^{2+}$ to the bath solution increased the instantaneous inward current in the CD20+ cells. Reduced bath $Ca^{2+}$ or $Ba^{2+}$ addition (FIG. 3B) did not alter the whole cell currents of CD20−Jurkat T cells in which the CD20-associated current component was absent. Intracellular free calcium concentrations were measured on CD20 transfected and control transfected Jurkat cells with Fura-2. The CD20 transfected cells had twice the free [$Ca^{2+}$]$_i$.

These results show that B lymphocyte cell surface protein CD20 functions physiologically as a plasma membrane $Ca^{2+}$ channel or an obligate regulator of a $Ca^{2+}$ channel. Antibody binding to CD20 increases inward $Ca^{2+}$ current, which is detectable following culture of lymphocytes in the presence of antibody, and therefore, antibody binding may inhibit cell cycle progression by sustaining a $Ca^{2+}$ influx above normal levels.

The following examples are intended to act as illustrations of the invention with no intention of limiting its scope.

EXAMPLE 1

The fact that CD20 functions in $Ca^{2+}$ mobility as described above provides a basis for a simple assay to detect an effect of an agonist or antagonist to CD20 on B lymphocyte function by measuring changes in calcium ion flux across the lymphocyte membrane. First, the resting calcium ion flux across the B lymphocyte membrane is determined. Next, the B lymphocyte is contacted with the agonist or antagonist to be tested. Finally, the change in calcium ion flux following contact with the tested agent is determined. One method to measure the ion channel flux is to use flow cytometry analysis of cells cultured with the $Ca^{2+}$ chelator and fluorochrome, Fura-2, an indicator that combines an 8-coordinate tetracarboxylate chelating site with a stilbene chromophore (Grynkiewicz et al., J. Biol. Chem. 260:3440 (1985)). In one experiment, CD20+ cells had a mean [$Ca^{2+}$]$_i$ of 124±47 nM (n=20) while the CD20− cells had a significantly lower (p<0.001) mean [$Ca^{2+}$]$_i$ of 58±45 nM (n=20). Uptake of extracellular $Ca^{2+}$ by both cell types showed that CD20+ cells accumulated intracellular calcium at a significantly (p=0.05) higher rate (2.44±1.30 nM/cell/sec) than did CD20− controls (0.3±0.23 nM/cell/sec).

EXAMPLE 2

Clark et al. (Proc. Nat'l Acad. Sci. USA 82:1766-1770 (1985)) describes two well characterized monoclonal antibodies that bind CD20, one inducing B cell proliferation and the other blocking cell cycle progression. These different physiological changes may be caused by differential effects of these antibodies on $Ca^{2+}$ transport. The assay method described in Example 1 can be used to categorize these differences so that additional populations of antibodies can be surveyed simply and easily.

EXAMPLE 3

Known pharmacologic $Ca^{2+}$ channel blocking agents, such as Bay K 8644, Verapamil, diltiazem, D-600, nipedipin and 4-aminopyridine, can be assayed for their specific inhibiting or augmenting effect on CD20 function.

EXAMPLE 4

Localization of the functional regions of the CD20 protein can be achieved by testing the effects of various agonists or antagonists to CD20 on modified CD20 molecules. A method of testing modified CD20 would include site-directed mutagenesis of CD20 cDNA, transformation of a CD20− cell line with the modified cDNA, expression of the modified CD20 protein encoded by the modified cDNA on the surface of cells of the CD20− cell line, and determination of the changes in calcium ion flux across the membrane of the transformed cell following exposure of the cell to the agonist or antagonist, a procedure analogous to that used by Eldefrawi et al (FASEB J. 1:262-271 (1987)) in targeting drugs towards receptors for γ-aminobutyric acid and voltage-dependent chloride channels. Knowledge of the functions of specific regions of CD20 can be applied to develop $Ca^{2+}$ channel blocking drugs which specifically target the CD20 cell surface protein without interfering with other cells of the immune system.

EXAMPLE 5

The method of the invention can be used to assay the effects of agonistic and antagonistic drugs on CD20 function in malignant B cells in order to clarify the role that regulating CD20 gene expression might have on limiting the growth advantage of CD20+ malignant cells.

Other embodiments are within the following claims.

We claim:

1. A method of testing the effect of an agonist or an antagonist to B lymphocyte cell surface protein CD20 on B lymphocyte function comprising
   determining calcium ion flux across the membrane of said B lymphocyte.
   contacting said B lymphocyte with said agonist or antagonist, and
   determining the change in calcium ion flux across said membrane after exposure of said B lymphocyte to said agonist or antagonist.

2. A method of testing the effect of an agonist or antagonist to B lymphocyte cell surface protein CD20 on modified cell surface protein CD20, said modifying being by site directed mutagenesis, said method comprising subjecting cDNA encoding cell surface protein CD20 to site directed mutagenesis to form modified CD20 cDNA, transforming a CD20− lymphocyte cell line with said modified CD20 cDNA, expressing a protein encoded by said modified cDNA on the surface of a transformed cell of said CD20− cell line, determining calcium ion flux across the membrane of said transformed cell expressing said protein encoded by said modified cDNA, contacting said transformed cell with an agonist or antagonist to B lymphocyte cell surface protein CD20, and determining the change in calcium ion flux across said membrane of said transformed cell after exposure of said transformed cell to said agonist or antagonist.

3. The method of claim 2 further comprising determining calcium ion flux across the membrane of a CD20+ B lymphocyte, contacting said CD20+ B lymphocyte with said agonist or antagonist to B lymphocyte cell surface protein CD20, determining the change in calcium ion flux across said membrane of said CD20+ B lymphocyte after exposure of said B lymphocyte to said agonist or antagonist, and comparing the change in calcium ion flux across said membrane of said transformed cell after exposure of said transformed cell of said agonist or antagonist with the change in calcium ion flux across said membrane of said B lymphocyte after exposure of said B lymphocyte to said agonist or antagonist.

4. The method of claim 1 or claim 2 wherein said agonist or antagonist comprises a ligand that binds to B lymphocyte cell surface protein CD 20.

5. The method of claim 1 or claim 2 wherein said agonist or antagonist comprises an antibody to B lymphocyte cell surface protein CD20.

6. The method of claim 5 wherein said B lymphocyte is contacted with said antibody for at least a period of time equivalent to one cell cycle before said change in said calcium ion flux is measured.

7. The method of claim 1 or claim 2 wherein said calcium ion flux is determined in terms of transmembrane current flow.

8. The method of claim 1 or claim 2 wherein said calcium ion flux is determined in terms of a change in cytosolic $Ca^{2+}$ concentration.

* * * * *